US009007595B2

United States Patent
Hanlon et al.

(10) Patent No.: US 9,007,595 B2
(45) Date of Patent: Apr. 14, 2015

(54) LAMP TEMPERATURE MANAGEMENT SYSTEMS AND METHODS FOR LIQUID CHROMATOGRAPHY ANALYZERS

(71) Applicant: PerkinElmer Health Sciences, Inc., Waltham, MA (US)

(72) Inventors: Gregory Hanlon, Windsor, CT (US); Timothy Neal, Harwinton, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 137 days.

(21) Appl. No.: 13/781,183

(22) Filed: Feb. 28, 2013

(65) Prior Publication Data

US 2014/0104598 A1    Apr. 17, 2014

Related U.S. Application Data

(60) Provisional application No. 61/792,596, filed on Feb. 8, 2013, provisional application No. 61/713,393, filed on Oct. 12, 2012.

(51) Int. Cl.
*G01N 21/00* (2006.01)
*G01N 21/01* (2006.01)
(Continued)

(52) U.S. Cl.
CPC . *G01N 21/01* (2013.01); *G01J 3/10* (2013.01); *G01J 3/0286* (2013.01); *G01N 30/74* (2013.01)

(58) Field of Classification Search
CPC ............... G01N 2015/0073; G01N 2015/008; G01N 2015/0084; G01N 35/1004; G01N 35/1079; G01N 2015/1062; G01N 2015/1486; G01N 2035/00891; G01N 15/1484; G01N 35/00663; G01N 35/1002; G01N 15/12
See application file for complete search history.

(56) References Cited

U.S. PATENT DOCUMENTS 3,916,195 A * 10/1975 Burch et al. .................. 250/345
5,153,679 A    10/1992 Gilby
(Continued)

FOREIGN PATENT DOCUMENTS

EP    1 182 443 A2    2/2002
EP    1 186 829 A1    3/2002
(Continued)

OTHER PUBLICATIONS

International Search Report and Written Opinion issued in corresponding PCT Application No. PCT/US2013/063926, mailed Jan. 9, 2014 (11 pages).
(Continued)

*Primary Examiner* — Michael P Stafira
(74) *Attorney, Agent, or Firm* — Myers Bigel Sibley & Sajovec, PA

(57) ABSTRACT

A liquid sample analyzer includes a flow cell, a light source, and a lamp temperature management system. The flow cell is configured to receive a flow of a liquid sample from a liquid sample source. The light source includes a lamp configured to emit light to illuminate the flow of the liquid sample in the flow cell. The lamp temperature management system includes: an air flow generator operable to generate a turbulent air flow to cool the lamp; a thermally conductive primary housing encapsulating the lamp such that a primary air gap is provided between the primary housing and the lamp; and a thermally conductive secondary housing surrounding the primary housing and configured to deflect the turbulent air flow away from the primary housing.

16 Claims, 15 Drawing Sheets

(51) Int. Cl.
*G01J 3/10* (2006.01)
*G01J 3/02* (2006.01)
*G01N 30/74* (2006.01)

(56) References Cited

U.S. PATENT DOCUMENTS

| | | |
|---|---|---|
| 5,184,192 A | 2/1993 | Gilby et al. |
| 5,416,879 A | 5/1995 | Liu |
| 5,444,807 A | 8/1995 | Liu |
| 5,608,517 A | 3/1997 | Munk |
| 6,188,813 B1 | 2/2001 | Dourdeville et al. |
| 6,314,227 B1 | 11/2001 | Nath |
| 6,526,188 B2 | 2/2003 | Dourdeville et al. |
| 6,542,231 B1 | 4/2003 | Garrett |
| 6,678,051 B2 | 1/2004 | Gerner et al. |
| 6,734,961 B2 | 5/2004 | Gerner et al. |
| 7,005,090 B2 | 2/2006 | Mueller et al. |
| 7,259,840 B1 | 8/2007 | Gerner et al. |
| 7,298,472 B2 | 11/2007 | Gerner et al. |
| 7,362,429 B2 | 4/2008 | Gilby |
| 7,808,619 B2 | 10/2010 | Gerner et al. |
| 7,847,944 B2 | 12/2010 | Buettner et al. |
| 7,859,657 B2 | 12/2010 | Jeannotte et al. |
| 7,914,852 B2 | 3/2011 | Belz et al. |
| 2009/0009758 A1 | 1/2009 | Gilby |

FOREIGN PATENT DOCUMENTS

| | | |
|---|---|---|
| GB | 1 515 632 A | 6/1978 |
| JP | 2001 126529 A | 5/2001 |
| JP | 2009 175006 A | 8/2009 |

OTHER PUBLICATIONS

Starna® Flow Cells for Spectophotometers, Retrieved Aug. 3, 2012 from URL http://www.starna.com/ukhome/d_cells/d_cells_s/flow/xflow.html , 3 pages.

* cited by examiner

US 9,007,595 B2

LAMP TEMPERATURE MANAGEMENT SYSTEMS AND METHODS FOR LIQUID CHROMATOGRAPHY ANALYZERS

RELATED APPLICATION(S)

The present application claims the benefit of and priority from U.S. Provisional Patent Application No. 61/762,596, filed Feb. 8, 2013, and U.S. Provisional Patent Application Ser. No. 61/713,393, filed Oct. 12, 2012, the disclosures of which are incorporated herein by reference in their entireties.

FIELD

The present technology relates to liquid sample analyzers and lamp temperature management therefor.

BACKGROUND

A deuterium light source is commonly used in liquid chromatography (e.g., LC PDA) applications as an Ultra Violet (UV) light source. Wavelength ranges of down to 190 nm and up to 700 nm are common in these types of applications. Typically, optical intensity varies with temperature changes and, thus, slight variations in bulb temperature can adversely affect noise and drift in the instrument leading to inaccurate or noisy readings. These types of lamps typically operate at relatively high temperatures (up to 290 deg. C.) and thereby require active cooling. Typically, forced convection by means of a fan is sufficient to keep the lamp from overheating.

SUMMARY

According to embodiments of the present technology, a liquid sample analyzer includes a flow cell, a light source, and a lamp temperature management system. The flow cell is configured to receive a flow of a liquid sample from a liquid sample source. The light source includes a lamp configured to emit light to illuminate the flow of the liquid sample in the flow cell. The lamp temperature management system includes: an air flow generator operable to generate a turbulent air flow to cool the lamp; a thermally conductive primary housing encapsulating the lamp such that a primary air gap is provided between the primary housing and the lamp; and a thermally conductive secondary housing surrounding the primary housing and configured to deflect the turbulent air flow away from the primary housing.

In some embodiments, the primary housing defines a lamp chamber containing the lamp and the lamp chamber is fluidly sealed from the exterior of the primary housing.

The liquid sample analyzer may include a buffer chamber defined by and between the primary housing and the secondary housing. In some embodiments, the primary housing includes thermal fins extending into the buffer chamber to facilitate heat transfer from the lamp chamber to the buffer chamber. In some embodiments, the buffer chamber is fluidly sealed from the turbulent air flow generated by the air flow generator. In some embodiments, the lamp temperature management system is configured such that, in use, a laminar air flow is generated in the buffer chamber.

The liquid sample analyzer may include a feed duct for directing the turbulent air flow at the secondary housing.

In some embodiments, the primary housing includes a window opening fluidly sealed by a transparent lens, and the light source is configured to emit light from the lamp through the lens to the flow cell. In some embodiments, the liquid sample analyzer includes a mirror disposed in the primary housing and configured to direct light from the lamp through the lens.

According to some embodiments, the liquid sample analyzer includes a source optical fiber configured and operatively connected between the primary housing and the flow cell to transmit light from the lamp to the flow cell.

In some embodiments, the primary housing and the secondary housing are each formed of metal.

The lamp may be a deuterium lamp.

In accordance with some embodiments: the primary housing defines a lamp chamber containing the lamp and the lamp chamber is fluidly sealed from the exterior of the primary housing; a buffer chamber is defined by and between the primary housing and the secondary housing; the primary housing includes thermal fins extending into the buffer chamber to facilitate heat transfer from the lamp chamber to the buffer chamber; the buffer chamber is fluidly sealed from the turbulent air flow generated by the air flow generator; the lamp temperature management system is configured such that, in use, a laminar air flow is generated in the buffer chamber; the primary housing includes a window opening fluidly sealed by a transparent lens; and the light source is configured to emit light from the lamp through the lens to the flow cell.

The liquid sample analyzer may further include a spectrometer optically connected to the flow cell to receive light from the flow cell, and a liquid sample source to supply the flow of the liquid sample to the flow cell.

According to method embodiments of the technology, a method for analyzing a liquid sample includes providing a liquid sample analyzer including: a flow cell configured to receive a flow of a liquid sample from a liquid sample source; a light source including a lamp configured to emit light to illuminate the flow of the liquid sample in the flow cell; and a lamp temperature management system. The lamp temperature management system includes: an air flow generator operable to generate a turbulent air flow to cool the lamp; a thermally conductive primary housing encapsulating the lamp such that a primary air gap is provided between the primary housing and the lamp; and a thermally conductive secondary housing surrounding the primary housing and configured to deflect the turbulent air flow away from the primary housing. The method further includes generating a turbulent air flow using the air flow generator and directing the turbulent air flow onto the secondary housing to cool the secondary housing, thereby cooling the primary housing, and thereby cooling the lamp.

In some embodiments, the primary housing defines a lamp chamber containing the lamp and the lamp chamber is fluidly sealed from the exterior of the primary housing.

In some embodiments, liquid sample analyzer includes a buffer chamber defined by and between the primary housing and the secondary housing.

In some embodiments, the primary housing includes thermal fins extending into the buffer chamber to facilitate heat transfer from the lamp chamber to the buffer chamber.

According to some embodiments, the buffer chamber is fluidly sealed from the turbulent air flow generated by the air flow generator.

In some embodiments, the lamp temperature management system is configured such that, in use, a laminar air flow is generated in the buffer chamber.

Further features, advantages and details of the present technology will be appreciated by those of ordinary skill in the art from a reading of the figures and the detailed description of

DETAILED DESCRIPTION

Figure 1A:
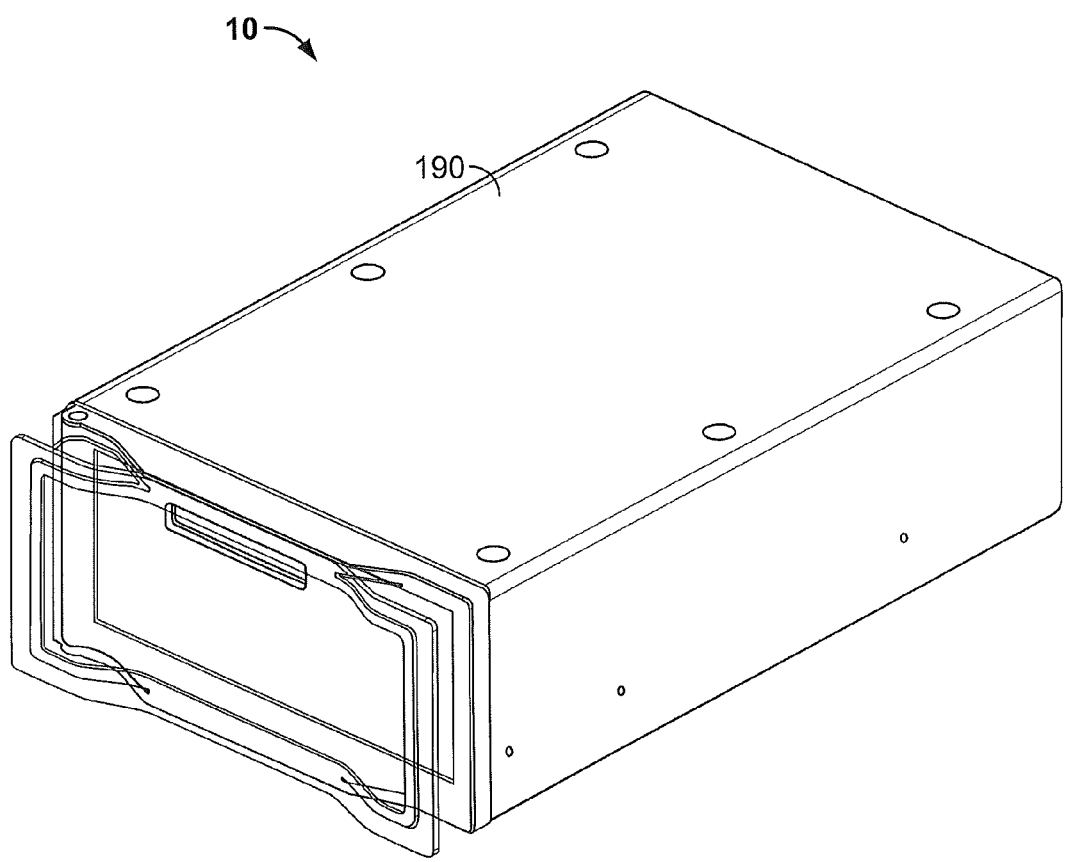
FIG. 1A is a front perspective view of a liquid sample analyzer according to embodiments of the technology.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc, may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

As discussed above, lamps used for illumination in liquid chromatography are typically actively cooled by forced convection (e.g., by means of a fan). A problem with direct forced convection is that turbulent air flow around the lamp and the lamp enclosure can lead to micro gradients in the surface temperature of the lamp bulb. These thermal gradients have been shown to increase the overall levels of noise produced by the lamp and are a detriment to the system.

According to embodiments of the present technology, a lamp temperature management system and method are provided for cooling a lamp (e.g., a deuterium lamp) of a light source in a spectroscopic liquid analyzer system. The method and system operate to remove sufficient heat energy from the lamp in order to maintain the lamp at a proper temperature, while also reducing the generation of thermal gradients in the surface temperature of the lamp bulb and providing higher levels of lamp stability.

In accordance with embodiments of the present technology, a liquid sample analyzer includes a light source, including a lamp, and a lamp temperature management system. The lamp temperature management system includes a thermally conductive primary housing, a thermally conductive secondary housing, and an air flow generator. The lamp is mounted in a primary or lamp chamber of the primary housing with an air gap provided between the lamp and the primary housing. This air gap acts as a thermal buffer and enables laminar convection heat transfer as the primary mode of heat energy removal from the lamp. The secondary housing surrounds the primary housing, and the secondary and primary housing define a secondary air gap therebetween. The secondary housing serves as a barrier between the primary housing and a system environment surrounding the secondary housing. According to some embodiments, the lamp chamber is fluidly sealed off from the lamp housing environment (i.e., the secondary chamber). In some embodiments, the lamp housing includes thermal fins extending outwardly into the surrounding lamp housing environment to facilitate thermal transfer to the lamp housing environment.

The air flow generator generates a flow of air that passes over the outer surfaces of the secondary housing and may also be circulated through the system environment to cool other components (e.g., other electronics). The air flow generator may be a fan or other device operable to force air flow. Heat energy from the lamp environment (i.e., the lamp chamber) is conducted through the walls of the primary housing and the secondary housing and delivered into the forced convective turbulent flow stream of the system environment caused by the air flow generator. Because the air in the lamp chamber and the air in the secondary chamber are mechanically sealed or separated from the forced air flow, the mechanical energy of the forced air flow is not imparted to the air in the lamp and secondary chambers. Moreover, the secondary chamber serves to provide a more uniformly distributed temperature profile or gradient at the outer surfaces of the primary housing. For example, while the secondary housing may have relatively cool and hot regions (e.g., with cooler regions being preferentially cooled by the forced air flow as a result of the system configuration), the resulting temperature gradients may induce a flow (e.g., a laminar flow) of the air in the secondary chamber. This induced air flow may serve to ameliorate or flatten the temperature profile at the outer surfaces of the primary housing.

By transferring and removing heat energy from the lamp as described above, the surface temperature of the lamp can remain very uniform throughout operation and is unaffected or less affected by slight changes in external temperature or fan velocity gradients.

Accordingly, the lamp temperature management system of the present technology can cool the lamp and at the same time set up a laminar convective flow around the primary housing, greatly reducing thermal gradients and leading to higher levels of lamp stability. In addition, the lamp temperature management system can allow for more rapid temperature stabilization for quick use of the instrument.

Figure 1B:
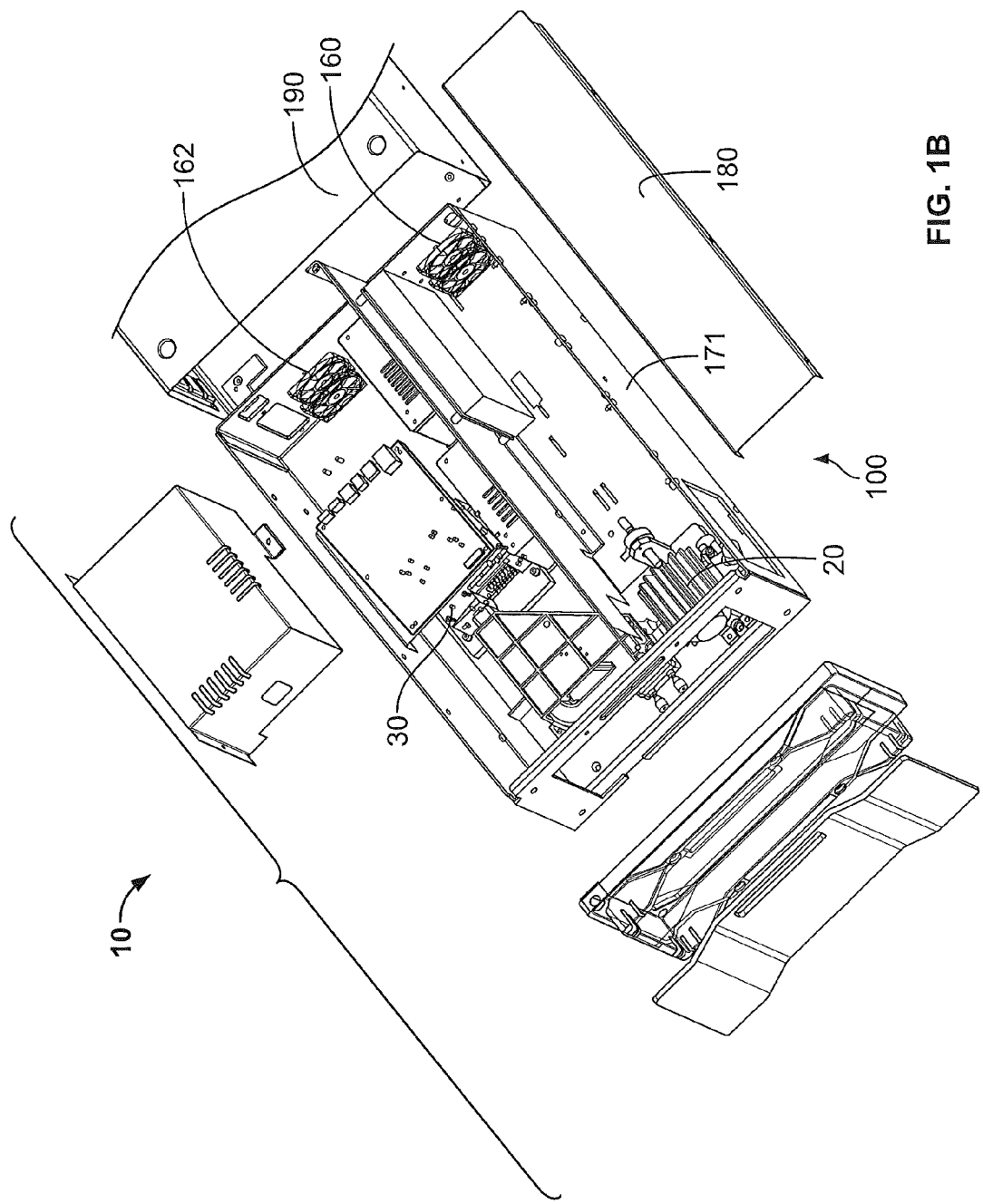
FIG. 1B is an exploded, front perspective view of the liquid sample analyzer of FIG. 1A.
Figure 9:
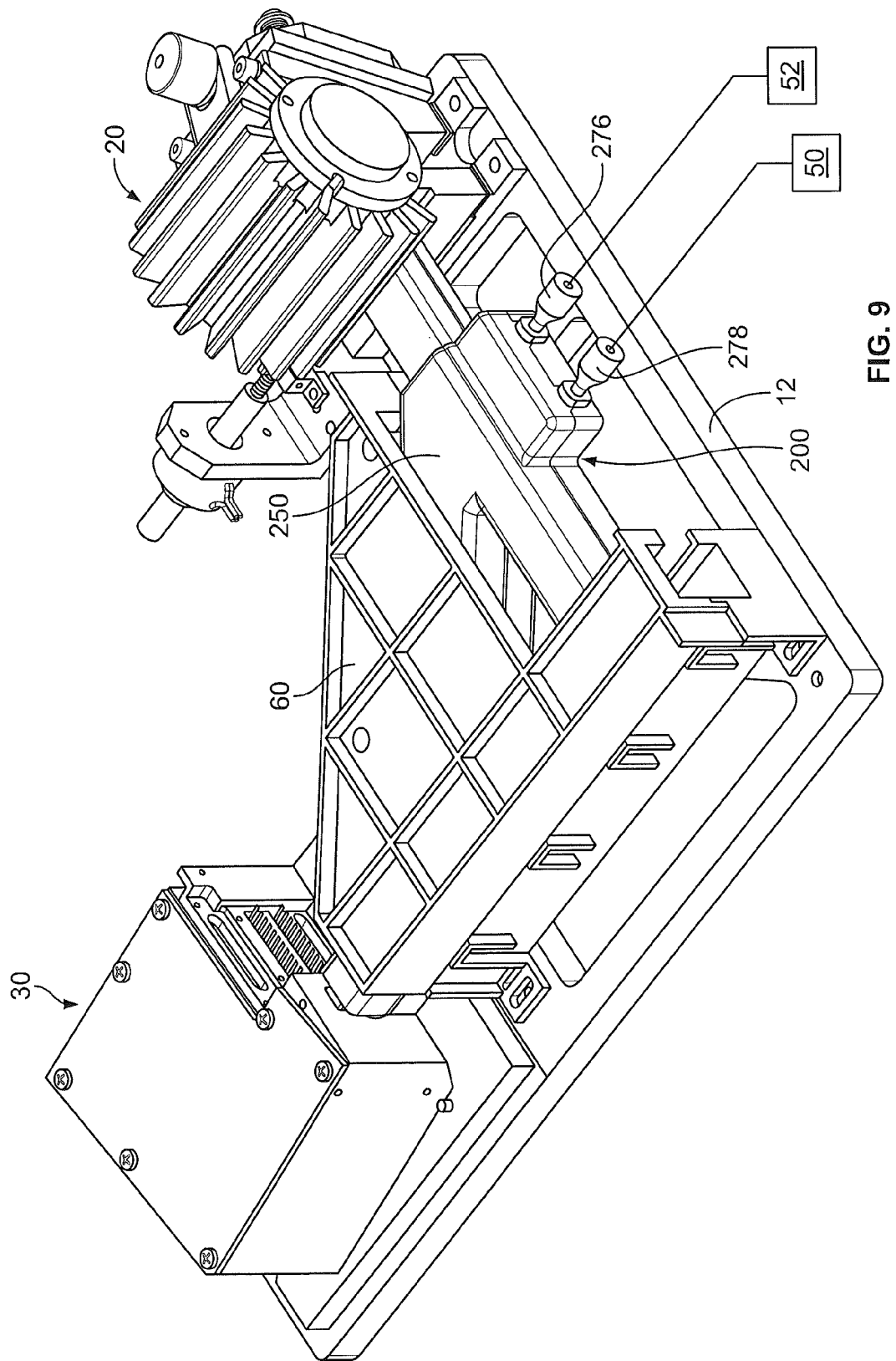
FIG. 9 is a perspective view of a subassembly of the liquid sample analyzer of FIG. 1A including a detector, the light source, a flow cell module, a base, a carrier tray, a liquid sample source, and a liquid sample receiver.
Figure 10:
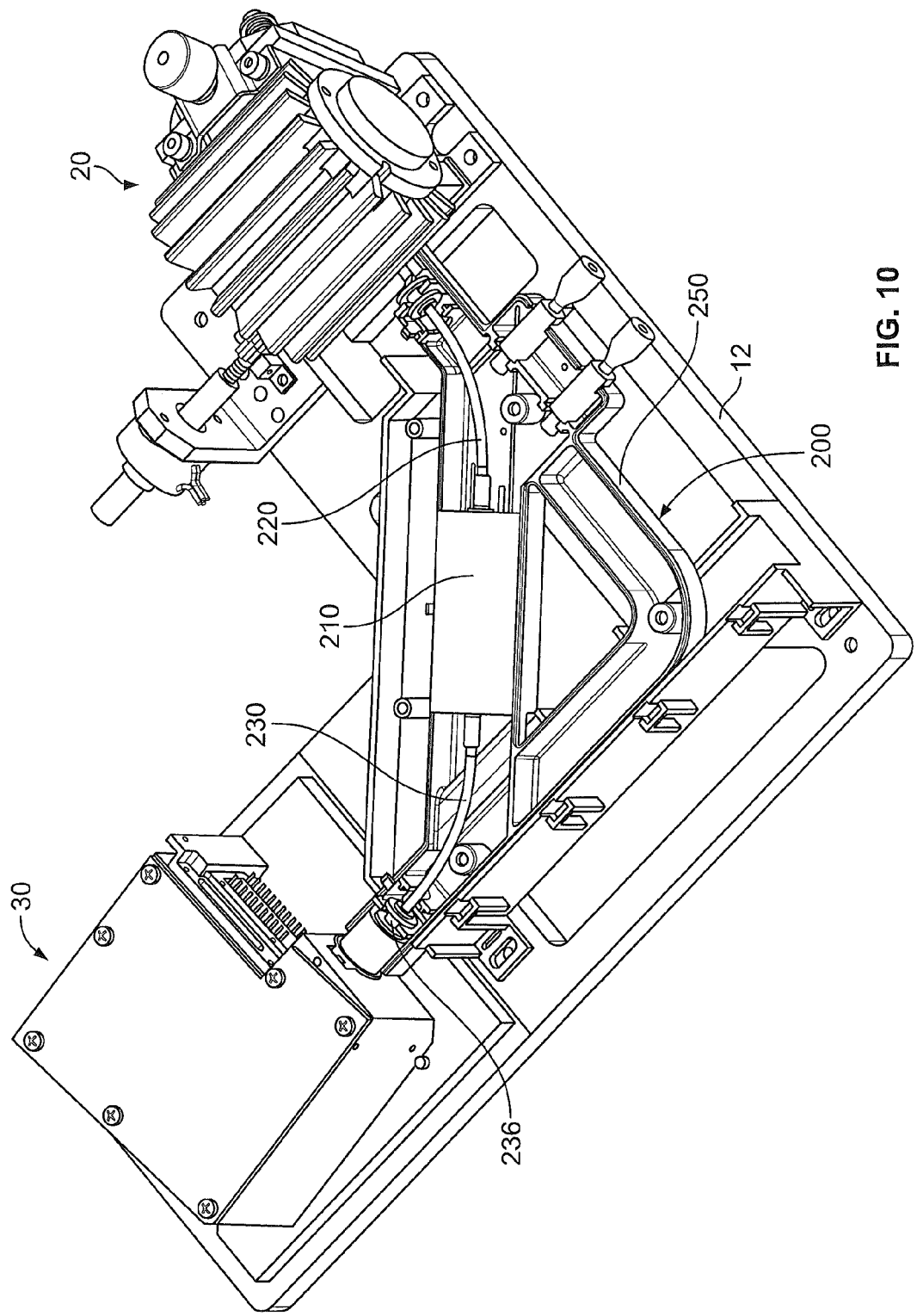
FIG. 10 is a fragmentary, perspective view of the subassembly of FIG. 9.
Figure 11:
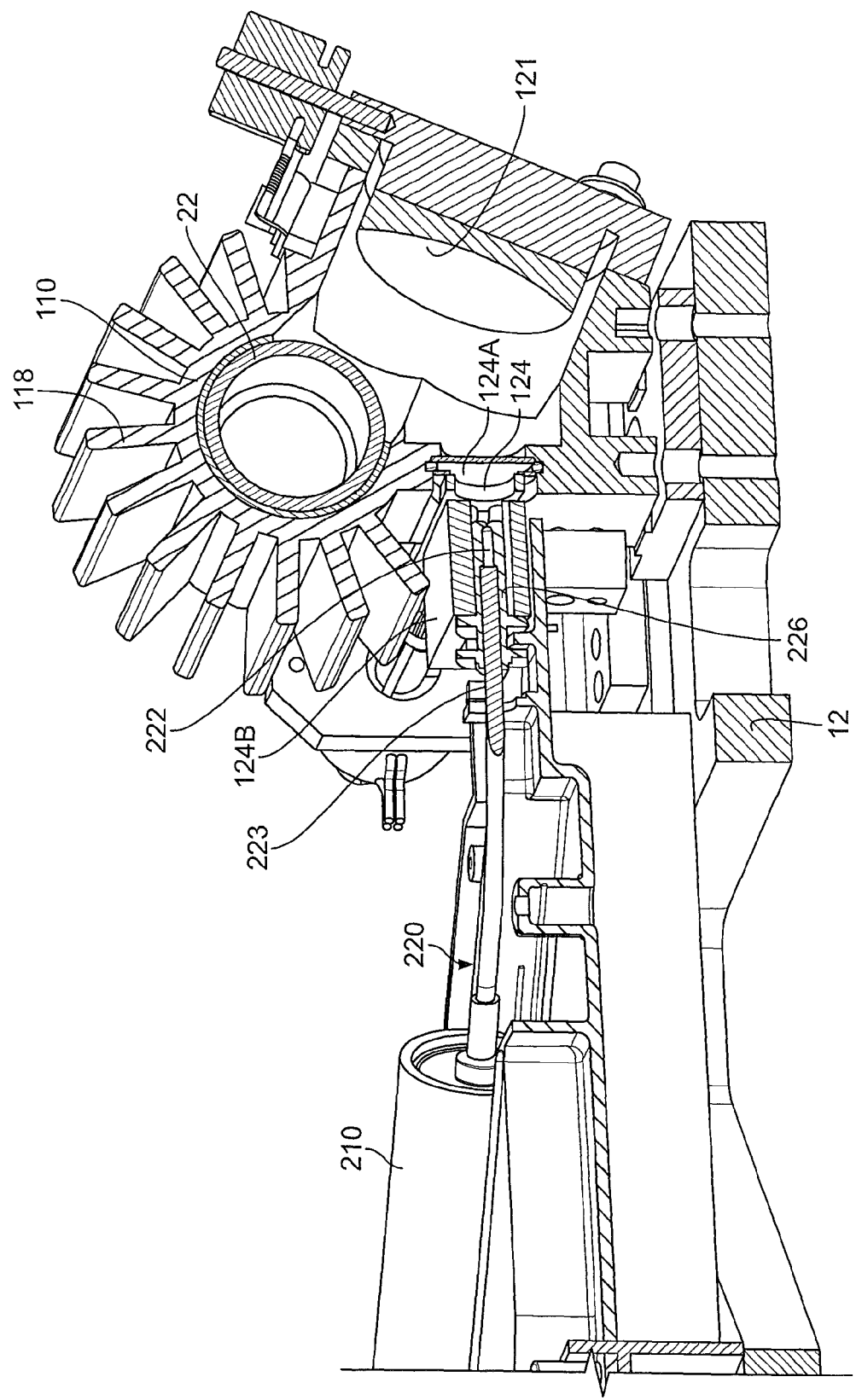
FIG. 11 is a further fragmentary, perspective view of the subassembly of FIG. 9.
Figure 12:
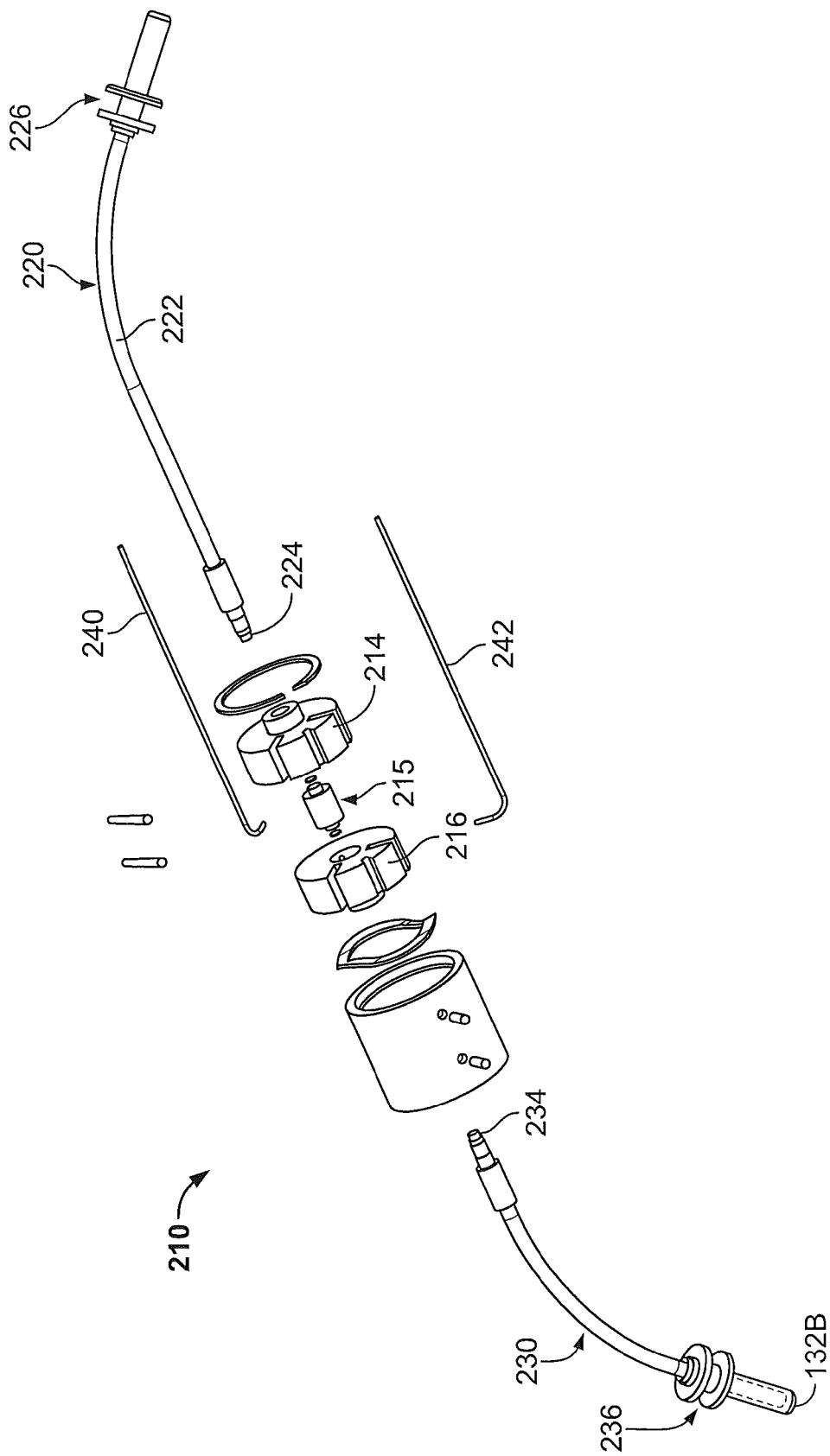
FIG. 12 is an exploded, perspective view of a flow cell forming a part of the flow cell module of FIG. 9.
Figure 13:
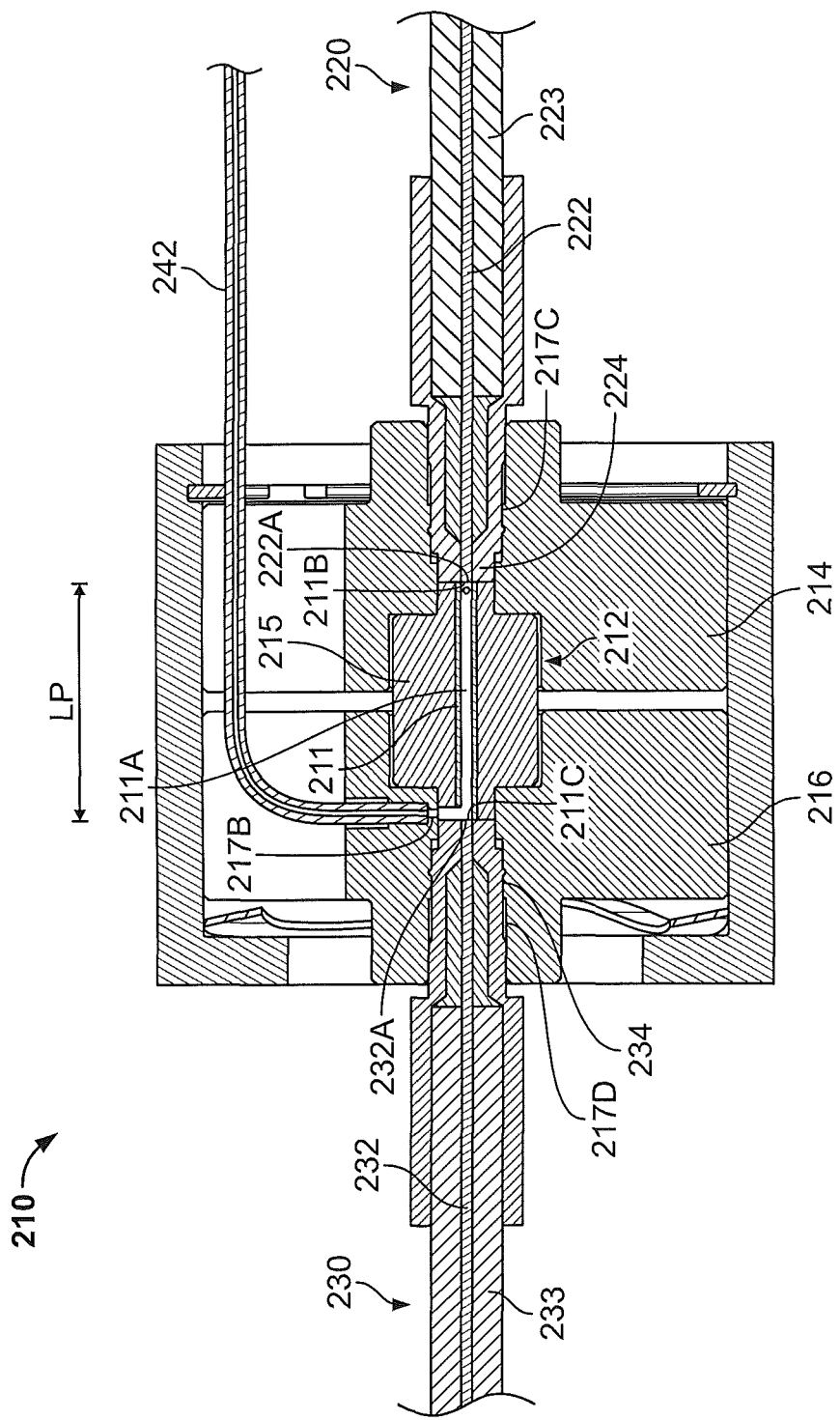
FIG. 13 is a cross-sectional view of the flow cell of FIG. 12.
Figure 14:
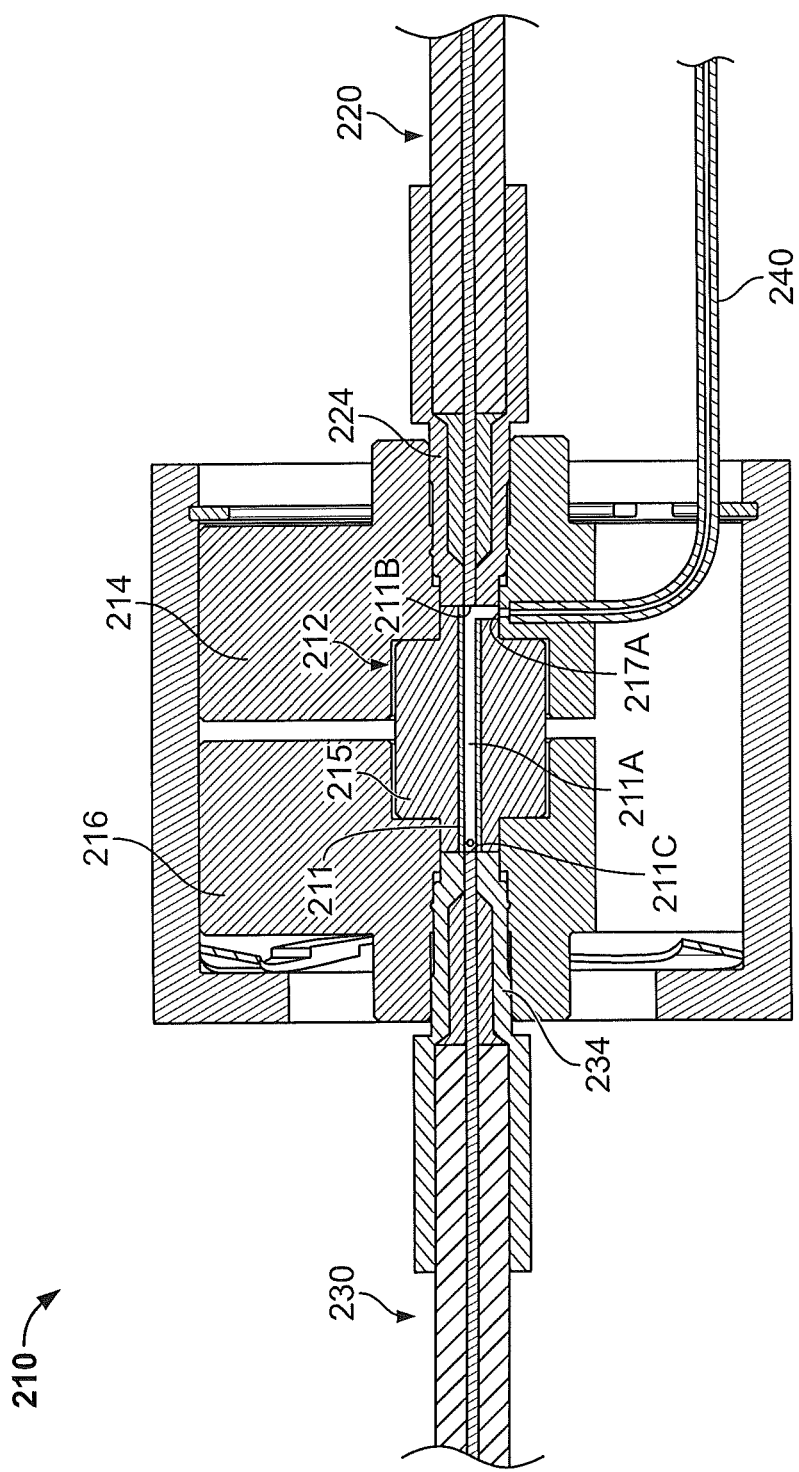
FIG. 14 is a cross-sectional view of the flow cell of FIG. 12.

With reference to the figures, a liquid sample analyzer 10 including a lamp temperature management system 100 according to embodiments of the technology is shown therein. The liquid sample analyzer 10 further includes a flow cell module 200 (FIGS. 10-14), a remote radiation or light source 20, a remote sensing device or detector 30 (FIGS. 1, 9 and 10), and a carrier tray 60 affixed to a shared base 12 (FIG. 10). The analyzer 10 further includes a remote liquid sample source 50 and a remote liquid sample receiver 52 (FIG. 9). The components 20, 30, 60, 100 and 200 are contained in a casing or system housing 170.

Figure 7:
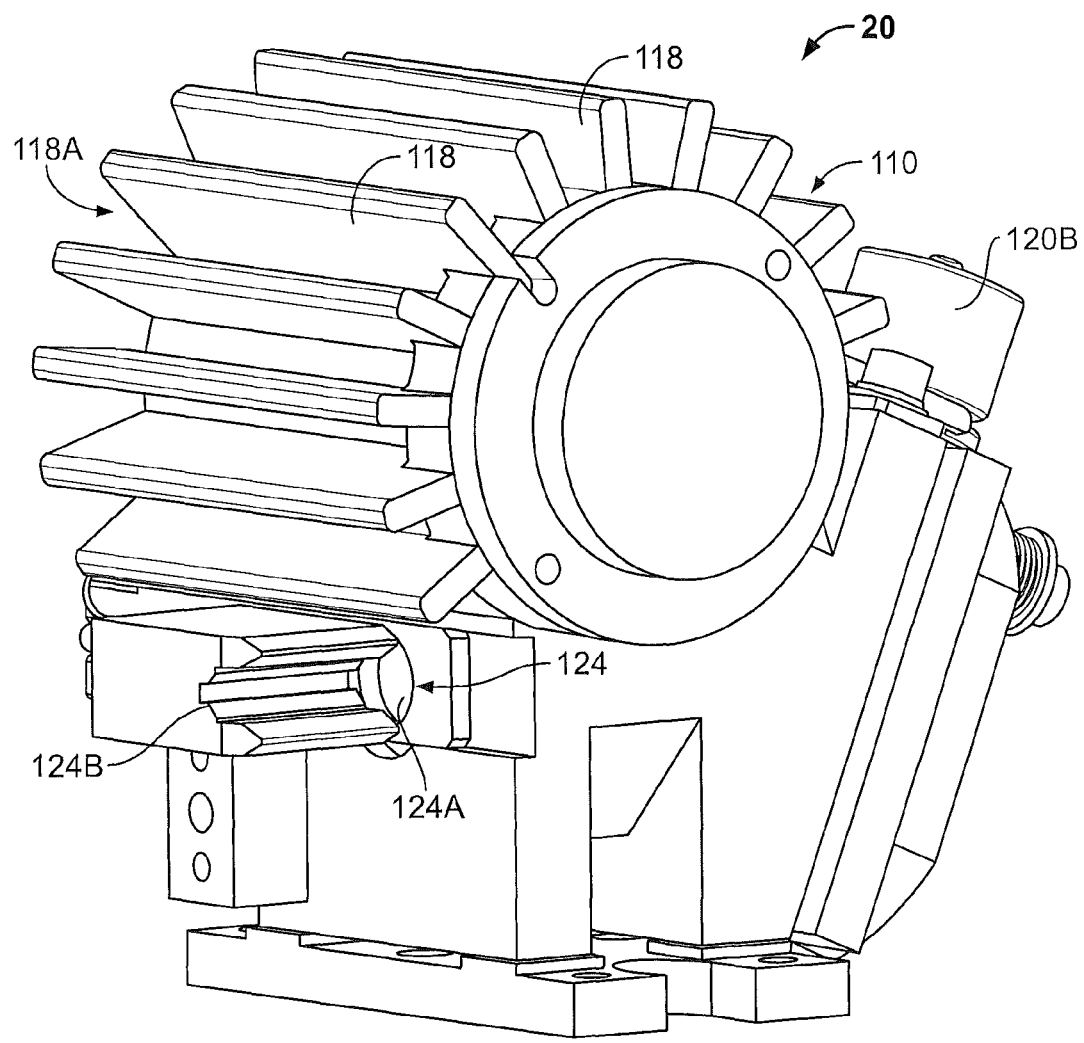
FIG. 7 is a front perspective view of the light source of FIG. 6.
Figure 8:
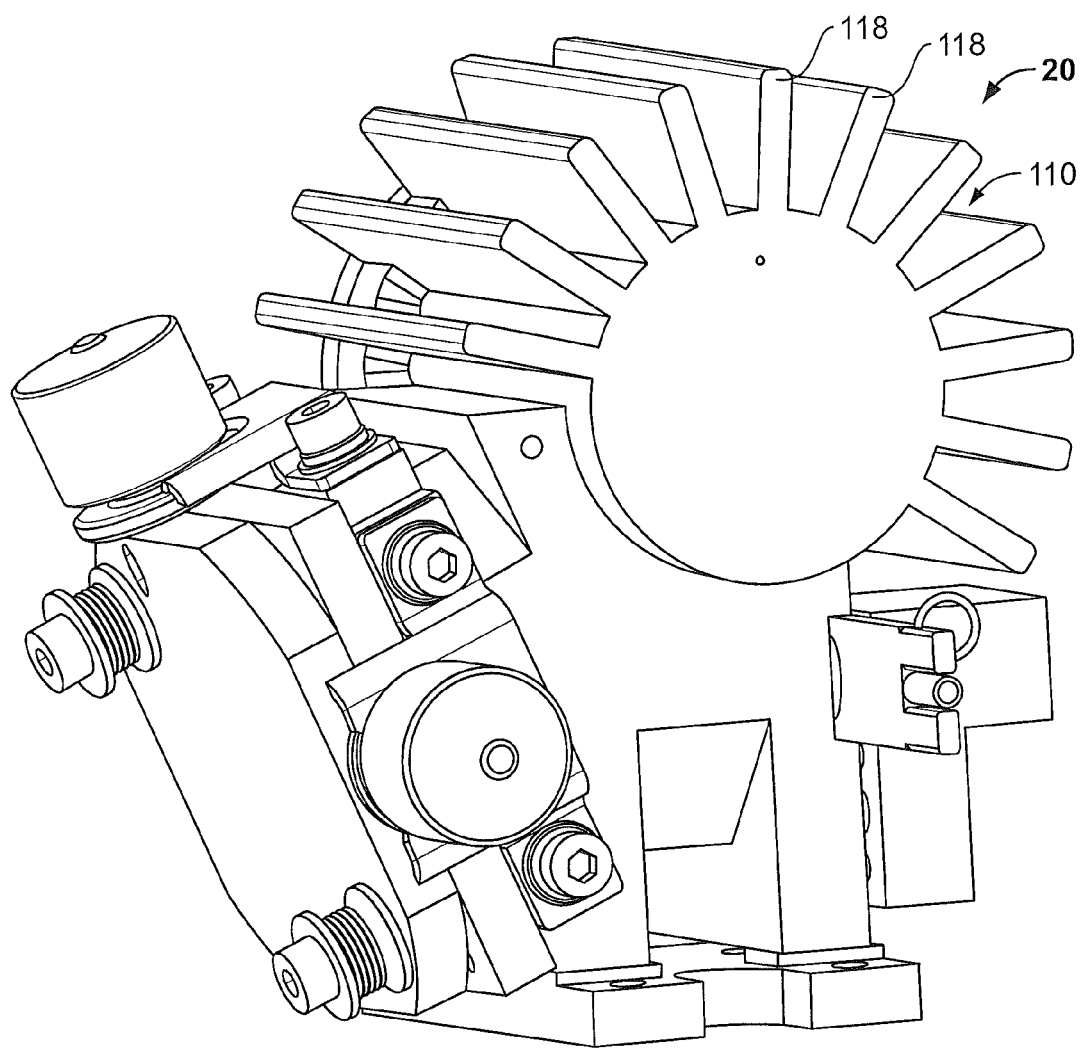
FIG. 8 is a rear perspective view of the light source of FIG. 6.

The light source 20 (FIGS. 6-8) includes a lamp 22 (FIG. 6) and a suitable power supply to power the lamp 22. The lamp 22 may be a lamp of any type suitable for spectroscopic analysis. According to some embodiments, the lamp 22 is a deuterium lamp. In some embodiments, the lamp 22 is a deuterium lamp having a wavelength output in the range of from about 190 nm to 700 nm and a total power output in the range of from about 25 to 35 watts.

The detector 30 may be any suitable sensing device or detector for spectroscopic analysis. According to some embodiments, the detector 30 is a spectrometer including a photodiode array (PDA). The detector 30 includes a fiber optic connector 32 for input of optical energy or signals for further processing.

The liquid sample source 50 may be any suitable source including a supply of the sample to be analyzed in a liquid solvent. According to some embodiments, the solvent is aqueous. The liquid sample receiver 52 may be a waste receptacle or a down line process. According to some embodiments, at least one of the liquid sample source 50 and the liquid sample receiver 52 is provided with a pump to generate a forced flow of the liquid sample through the flow cell module 200.

The carrier tray 60 is secured to the base 12 and defines a holding cavity, socket or slot 64 and a front opening 62 communicating with the slot 64.

The flow cell module 200 (FIGS. 12-14) includes a flow cell unit or assembly 210, a connectorized radiation input or source optical fiber 220, a connectorized radiation output or detector optical fiber 230, a liquid sample feed capillary tube 240, a liquid sample exit capillary tube 242, a module housing 250 (FIG. 9), a liquid sample feed connector 276, and a liquid sample exit connector 278. The components 210, 220, 230, 240, 242, 276, and 278 are mounted in the module housing 250, as discussed in more detail herein.

The source connectorized fiber 220 includes a flexible optical fiber or waveguide 222, a ferrule 224, and a termination 226. The optical fiber 222 may be an optical fiber including a solid glass core and a solid glass cladding and may be covered in a protective jacket 223. The ferrule 224 is mounted on one end of the optical fiber 222 such that an output end face 222A is exposed adjacent and substantially flush with an end face of the ferrule 224. The termination 226 is mounted on the opposite end of the optical fiber 222 such that an input end face 222B of the optical fiber 222 is exposed. In use, the termination 226 is installed proximate the light source 20 such that light from the light source 20 is directed into the optical fiber 222 through the end face 222B and transmitted through the fiber 222 and out of the fiber 222 through the end face 222A.

The detector connectorized fiber 230 includes a flexible optical fiber 232 (which may be covered in a protective jacket), a ferrule 234, and a termination 236. The ferrule 234 is mounted on an end of the optical fiber 232 such that an input end face 232A is exposed adjacent and substantially flush with an input end face of the ferrule 234. The termination 236 is mounted on the opposite end of the fiber 232 such that an output end face 232B of the fiber 232 is exposed. In use, the termination 236 is mated with the fiber optic connector 32 of the detector 30 to transmit light from the end face 232A to the detector 30.

The capillary tubes 240, 242 fluidly couple the flow cell assembly 210 to the liquid sample source 50 and the liquid sample receiver 52, respectively, via the connectors 276, 278.

In some embodiments, the flow cell assembly 210 includes a flow cell or liquid core waveguide 212 mounted in or between an entrance "T" member or joint member 214 and an exit "T" member or joint member 216, which are in turn mounted in a housing 218. The waveguide 212 may include a waveguide body 215 and a cladding layer 211 extending through the waveguide body 215. The inner surface of the cladding layer 211 defines a passage or bore 211A extending axially fully through the waveguide body 215 and terminating at opposed end openings 211B, 211C.

The flow cell assembly 210 includes a fluid feed port 217A fluidly connecting the feed tube 240 to the end opening 211B of the waveguide bore 211A and a fluid exit port 217B fluidly connecting the exit tube 242 to the end opening 211C of the waveguide bore 211A. The flow cell 210 also includes a source fiber receiving bore 217C that receives the ferrule 226 and positions the fiber output end face 222A adjacent the end opening 211B, and a detector fiber receiving bore 217D that receives the ferrule 234 and positions the fiber end face 232A adjacent the end opening 211C.

Figure 3:
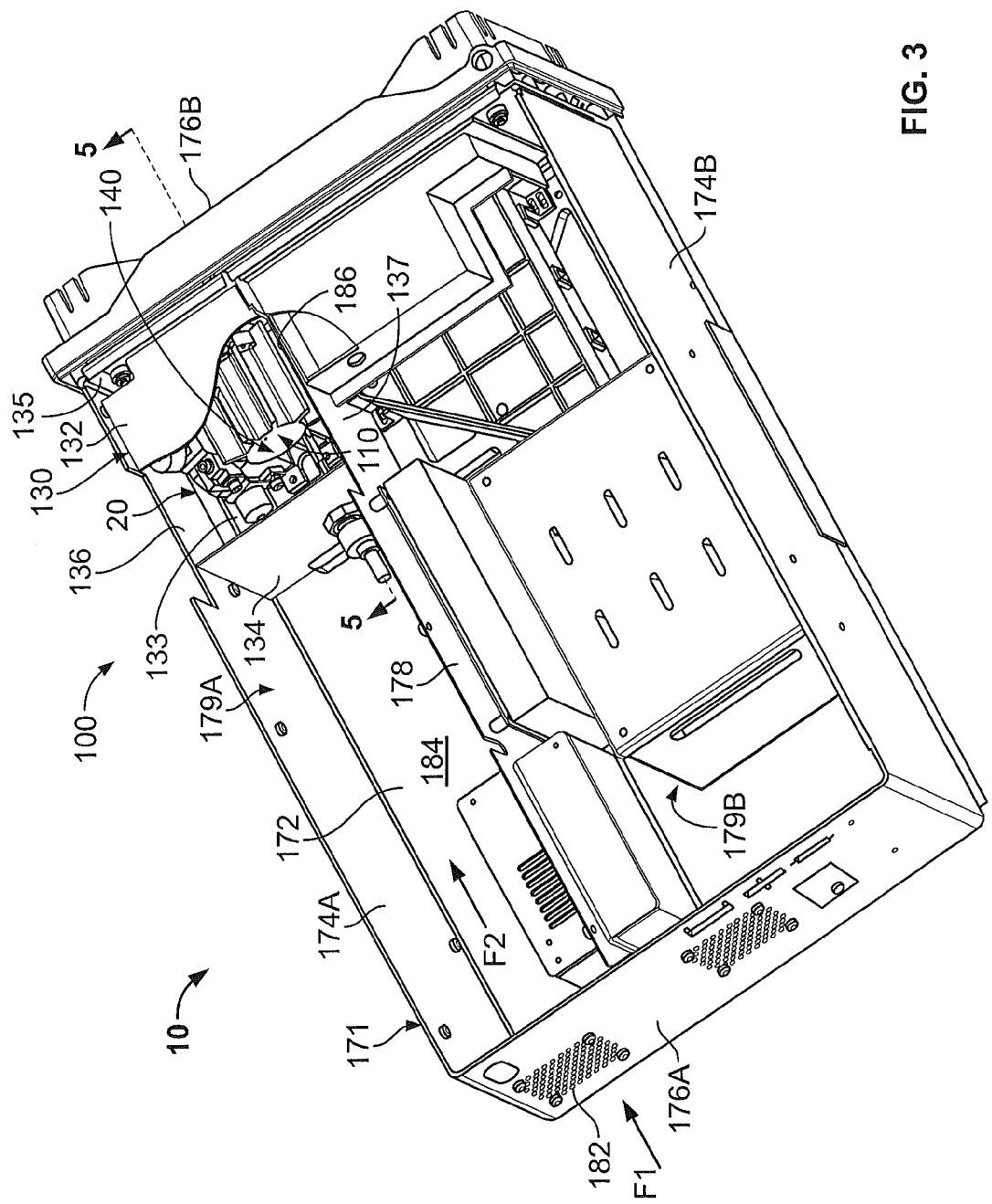
FIG. 3 is a fragmentary, rear perspective view of the liquid sample analyzer of FIG. 1A with the outer casing and a baffle wall thereof removed.
Figure 4:
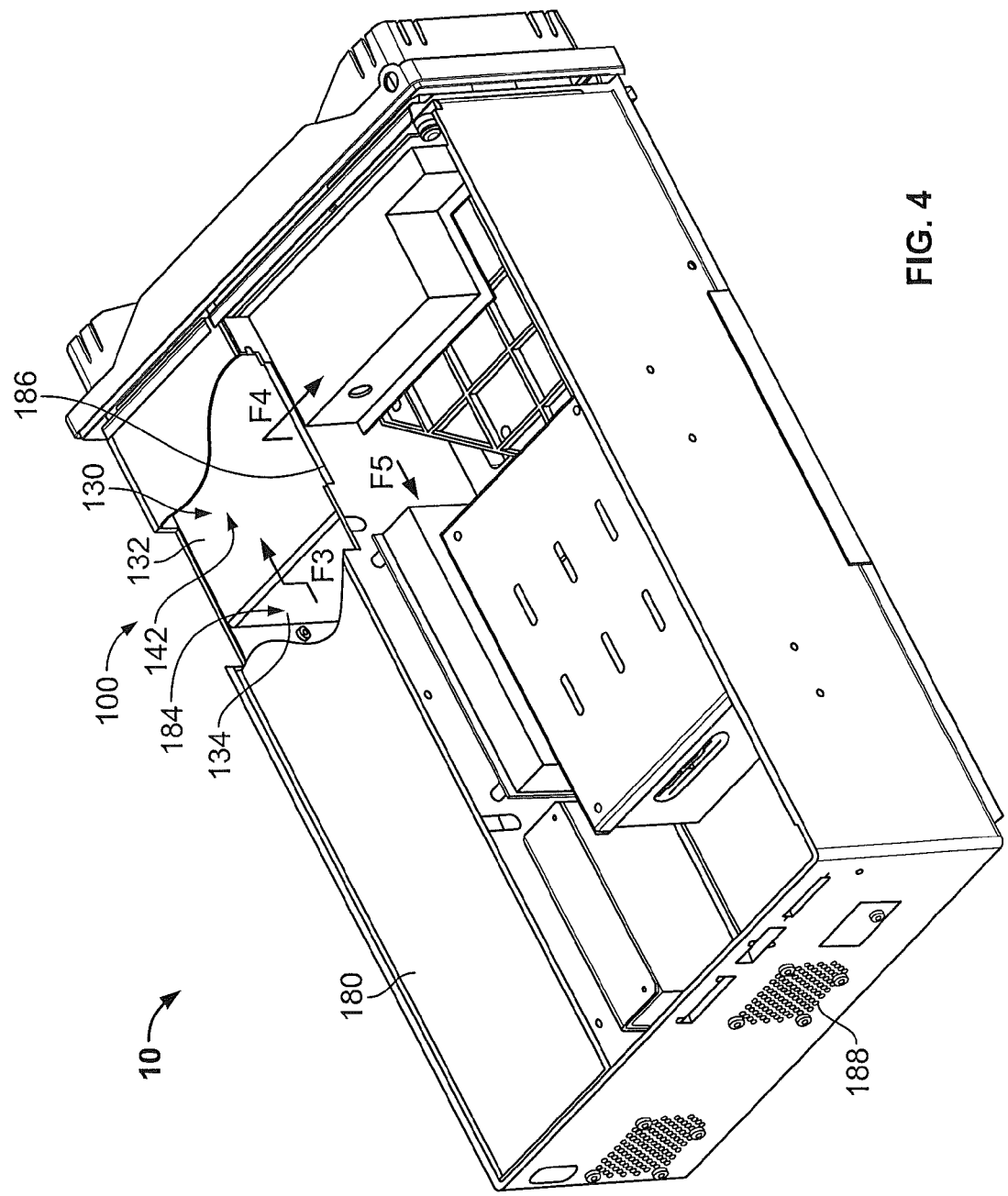
FIG. 4 is a fragmentary, rear perspective view of the liquid sample analyzer of FIG. 1A with the outer casing removed.

The lamp temperature management system 100 includes an inner or primary housing 110 (FIG. 3), an outer or secondary housing 130 (FIG. 4), one or more air flow generators 160, 162 (FIG. 1B) and portions of the system housing 170. In the illustrated embodiment, the air flow generators include an electrically powered fan 160 arranged to draw air into the housing 170 and an electrically powered fan 162 arranged to exhaust air from the housing 170.

The system housing 170 includes a base wall 172 (FIG. 3), opposed sidewalls 174A, 174B, opposed end walls 176A, 176B, a partition wall 178, a baffle or top duct wall 180, and an outer casing 190. The partition wall 178 defines a first chamber 179A and a second chamber 179B. The first chamber 179A contains the light source 20, the inner housing 110, the outer housing 130, and the fan 160. The detector 30, the carrier tray 60, and the flow cell module 200 are disposed in the second chamber 179B. The outer casing 190 and the walls 174A, 174B, 176A, 176B collectively fully encase the chambers 179A, 179B.

Figure 2:
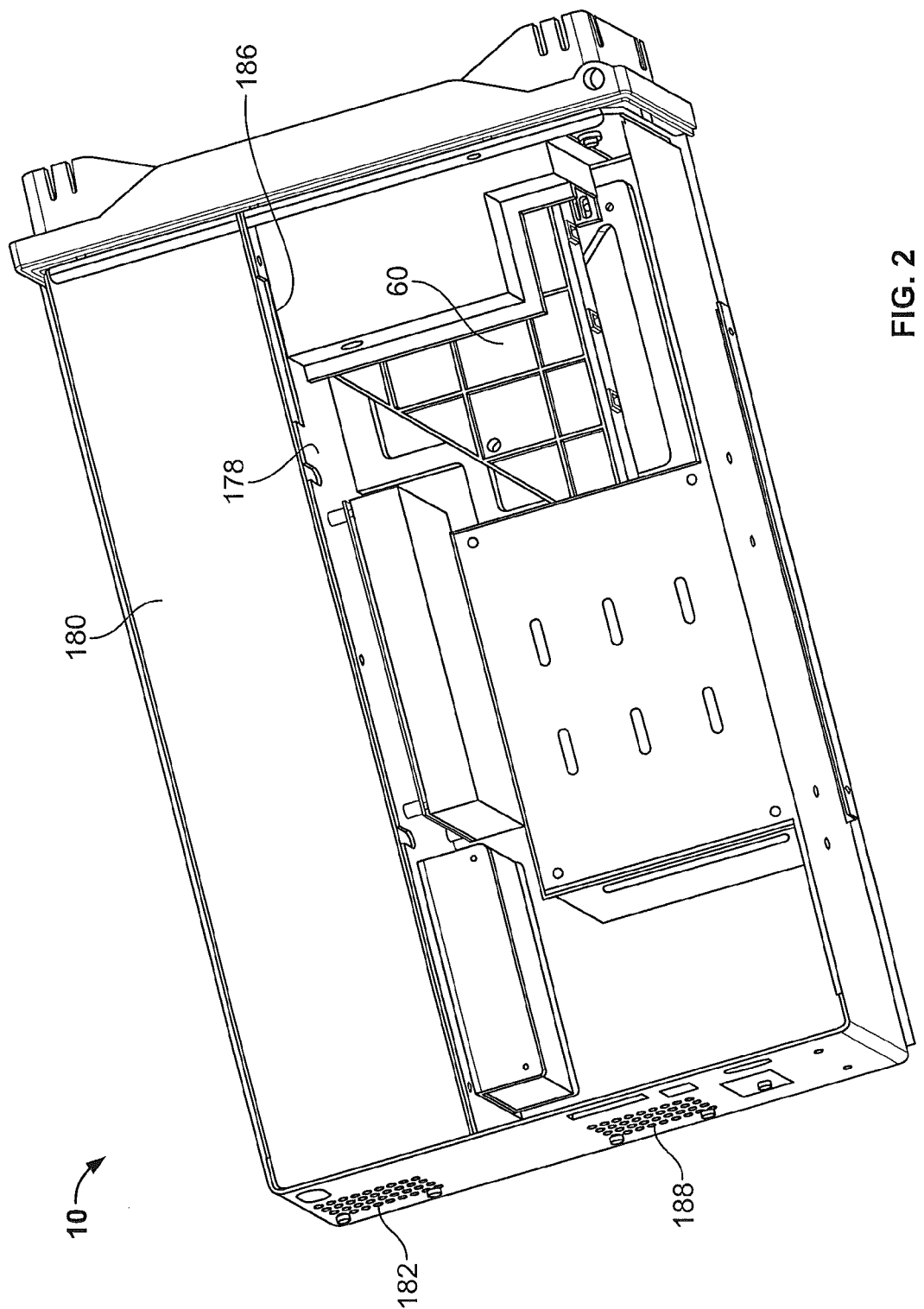
FIG. 2 is a rear perspective view of the liquid sample analyzer of FIG. 1A with an outer casing thereof removed.

An intake port 182 is defined in the end wall 176A adjacent the first chamber 179A. The walls 172, 174A, 178 and 180 define a feed duct 184 extending from the intake port 182 to a cross-over or connecting port 186 (FIGS. 2 and 4) defined in the partition wall 178. An exhaust port 188 is defined in the end wall 176A adjacent the second chamber 179B.

Figure 6:
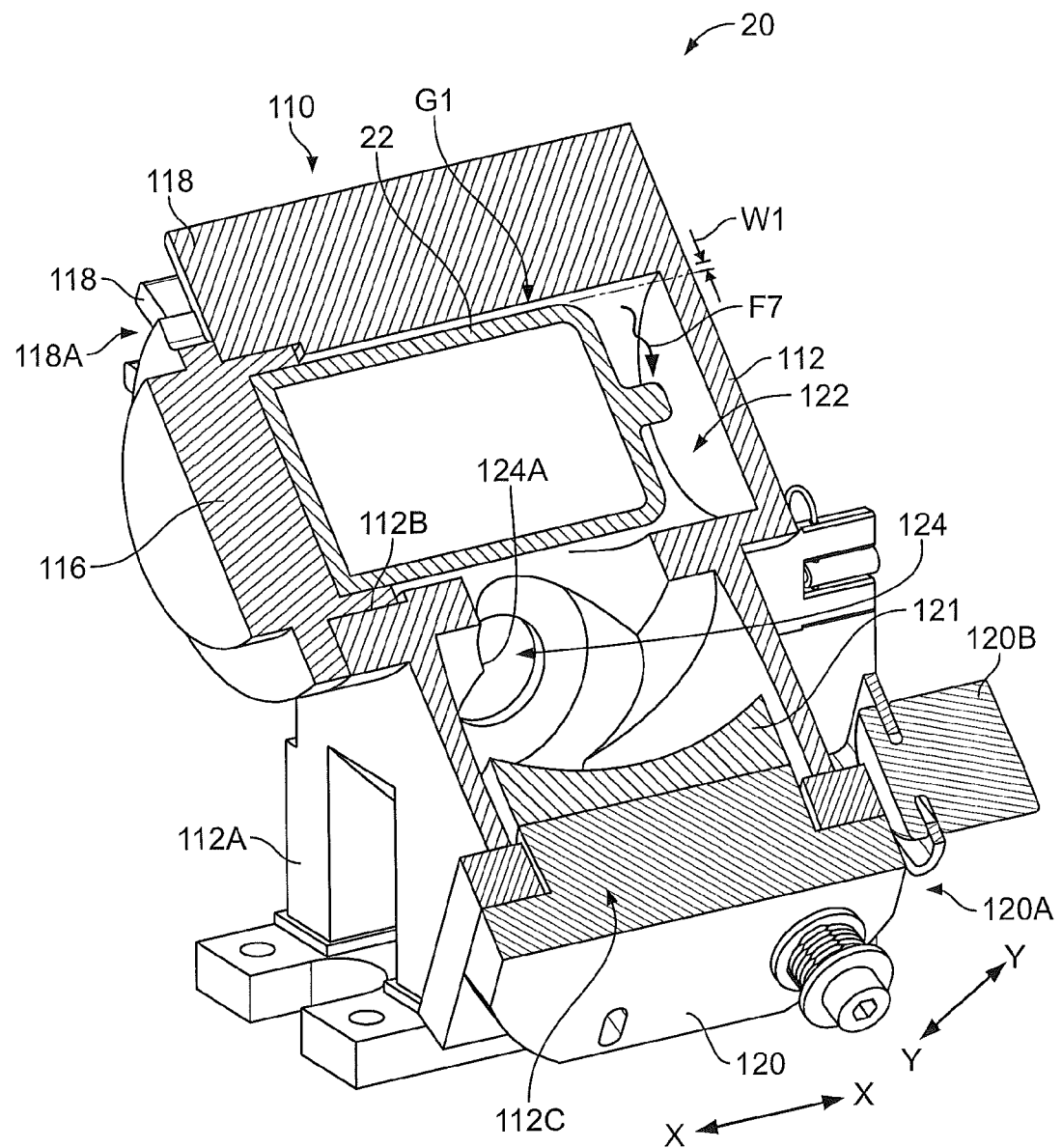
FIG. 6 is a cross-sectional, perspective view of a light source forming a part of the liquid sample analyzer of FIG. 1A.

With reference to FIG. 6, the primary housing 110 includes a body 112, a lamp holder 116 and a mirror carrier 120 collectively defining a lamp chamber 122. The lamp 22 is disposed in the lamp chamber 122.

The body 112 includes an integral base 112A (secured to the base 12), a lamp access opening 112B, a mirror opening 112C, and a window opening 124. A plurality of integral cooling fins 118 extend radially outwardly from the body 112 and define a plurality of substantially parallel cooling channels 118A therebetween.

The lamp holder 116 is removeably secured (e.g., by screw threads) in the lamp access opening 112B to seal the opening 112B. The lamp holder 116 may include an electrical connection for supplying electrical power to the lamp 22.

The mirror carrier 120 is slideably mounted at the mirror opening 112C to seal the opening 112C. A mirror 121 is mounted on the mirror carrier 120 for movement therewith. A mirror positioning mechanism 120A including adjustment knobs 120B is provided to translate the mirror 121 along each of an X axis and a Y axis relative to the lamp chamber 122. According to some embodiments, the mirror 121 is a concave mirror configured to focus and direct light from the lamp 22 through the window opening 124. A lens 124A is provided in the window opening 124 to seal the window opening 124 and in some embodiments to focus the light beam from the mirror 121. An alignment block 124B may be provided to receive and positively align the termination 226 of the flow cell assembly 210 with the window 124.

The body 112 and the fins 118 are formed of a thermally conductive material. According to some embodiments, the body 112 and the fins 118 are formed of a material having a thermal conductivity in the range of from about 100 W/m-k to 250 W/m-k. In some embodiments, the body 112 and the fins 118 are formed of metal, and in some embodiments, aluminum. According to some embodiments, the body 112 and the fins 118 constitute a monolithic structure. In some embodiments, the lamp holder 116 and the mirror carrier 120 are likewise formed of a thermally conductive material and in some embodiments, a metal (e.g., aluminum).

With the exception of the region of engagement between the lamp 22 and the lamp holder 116, the lamp 22 is surrounded by an air gap G1 (FIG. 6) between the outer surface of the lamp 22 and the inner surface of the inner housing 110. According to some embodiments, the air gap G1 has a width W1 (FIG. 6) of at least 0.05 inch and, in some embodiments, in the range of from about 0.1 to 0.125 inch.

Figure 5:
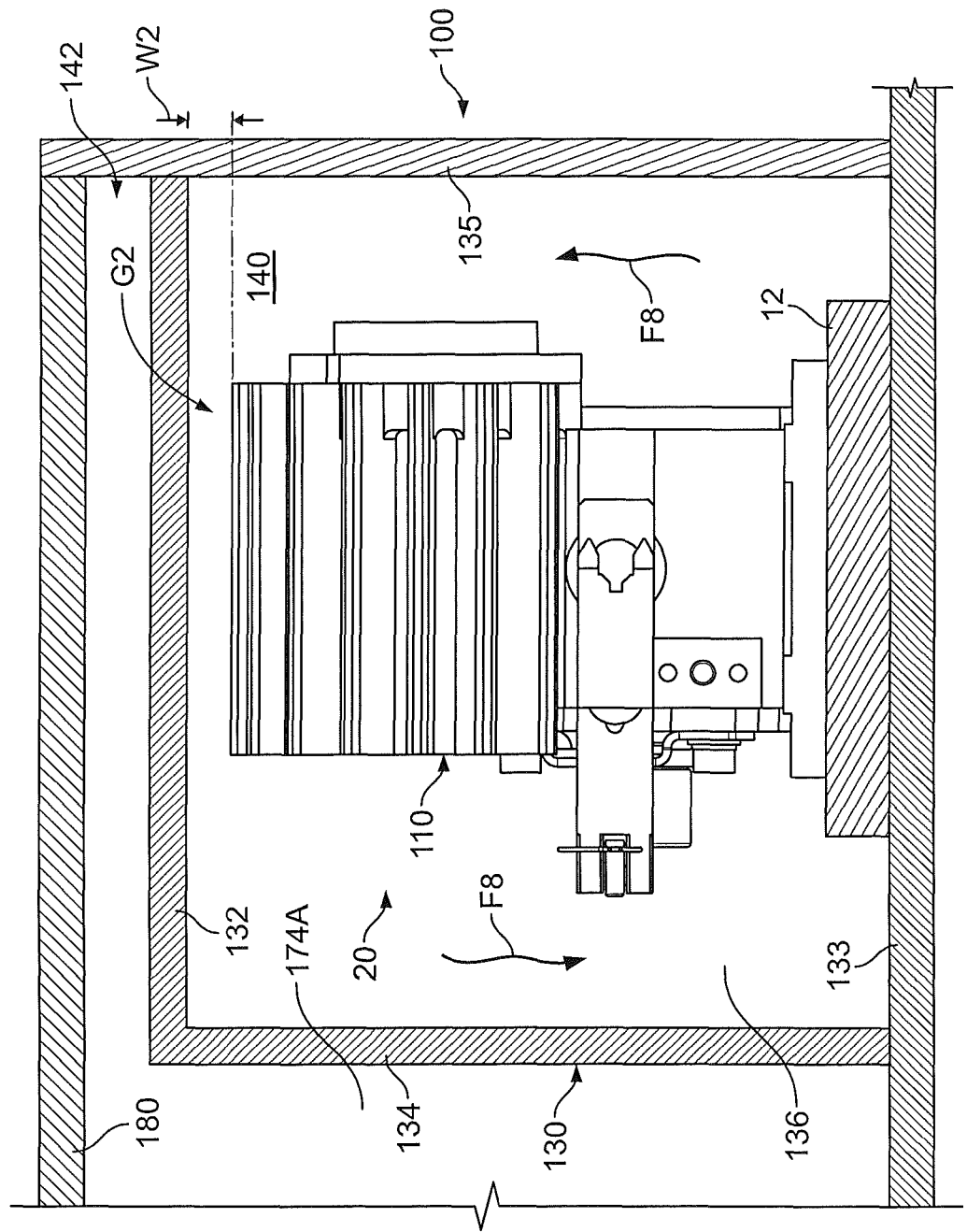
FIG. 5 is a cross-sectional view of the liquid sample analyzer of FIG. 1A taken along the line 5-5 of FIG. 3.

The secondary housing 130 (FIGS. 3-5) includes a top wall 132, a bottom wall 133, a front wall 134, a rear wall 135, an outer sidewall 136, and an inner sidewall 137. The bottom wall 132 may be a section of the base wall 172, the sidewall 136 may be a section of the sidewall 174A, and sidewall 137 may be a section of the partition wall 178. The secondary housing 130 defines a buffer chamber 140. A reduced height plenum 142 is defined between the top wall 132 and the top wall 180 and fluidly connects the feed duct 184 and the connecting port 186.

With the exception of the region of engagement between the base 112B and the base 12, the primary housing 110 is surrounded by an air gap G2. According to some embodiments, the air gap G2 has a width W2 of at least about 0.25 inch, and, in some embodiments, in the range of from about 0.5 to 1.5 inch. As shown, the outer housing 130 may be substantially box shaped. However, other configurations may be employed.

The outer housing 130 is formed of a thermally conductive material. According to some embodiments, the outer housing 130 is formed of a material as described above for the inner housing 110.

In use, as discussed below, the lamp 22 is powered to generate a light beam that is directed into the flow cell assembly 210 to enable spectroscopic analysis. In doing so, the lamp 22 generates excessive heat that must be removed to ensure proper operation of the lamp 22. To this end, the fan 160 and the fan 162 draw a flow F1 (FIG. 3) of air into the intake port 182 and generates a forced flow F2 of the air through the feed duct 184 toward the outer housing 130. According to some embodiments, the flow F2 has a volumetric flow rate in the range of from about 10 to 15 cubic feet per minute. The circulated air flows F3 (FIG. 4) over the outer housing 130, through the connecting port 186 (flow F4), through the chamber 179B (flow F5), and out through the exhaust port 188 (flow F6). The turbulent air flow is thus isolated or deflected away from the inner housing 110. The turbulent forced circulated air removes heat from and thereby cools the outer housing 130. Heat energy from the lamp 22 is, sequentially, transferred through the air gap G1 (in some embodiments, primarily by a laminar convective air flow F7 (FIG. 6)), conductively transferred through the inner housing 110, transferred through the air gap G2 (in some embodiments, primarily via a laminar convective air flow F8 (FIG. 5)), conductively transferred through the outer housing 130 and transferred into the forced convective turbulent air flow stream (F3) of the circulated air.

According to some embodiments and as shown, the lamp chamber 122 (i.e., the lamp environment) is substantially fully fluidly sealed from the buffer chamber 140. According to some embodiments, the buffer chamber 140 is also substantially fully fluidly sealed from the forced air flow (i.e., the system environment). In other embodiments, the buffer chamber 140 may be fluidly connected to the system environment, but configured such that turbulence from the forced air flow is substantially prevented or inhibited from introducing turbulence into the air in the buffer chamber 140. The air gap G1 acts as a thermal buffer and allows laminar convective heat transfer as the primary mode of heat energy removal from the lamp 22. Likewise, the air gap G2 may act as a thermal buffer and allow laminar convective heat transfer as the primary mode of heat removal from the inner housing 110. The fins 118 facilitate the thermal heat transfer to the buffer environment by increasing the total surface area and thereby increasing the rate of heat transfer. By transferring and removing heat from the lamp 22 in this way, the surface temperature of the lamp 22 can be maintained more spatially uniform throughout operation and will tend not to be affected by slight changes in external temperature or fan velocity gradients.

Because the lamp chamber 122 is sealed off from the system environment and the air circulated by the fans 160, 162, fresh air is prevented from entering the lamp chamber 122. In this way, the lamp temperature management system 100 can limit or reduce the generation of ozone in the lamp environment by the lamp 22. In general, ozone tends to absorb UV light and can thereby alter the intensity of the light emitted from the light source 20, and thereby create undesirable noise.

In order to achieve the foregoing benefits, a heat balance may be established from the lamp surface through to the system environment with consideration of system geometry and materials. The heat balance and operation may be dependent on the widths of the air gaps G1, G2, the masses of the housings 110, 130, the quantity and sizes of the fins 118, the volumes of air contained in the chambers 122, 140, the thicknesses of the walls of the housings 110, 130, and the air flow velocity of the air flow F3.

In an exemplary use, a flow of the liquid sample is pumped or otherwise driven from the liquid sample source 50, through the feed connector 276, through the feed tube 240, through the waveguide 212 (more particularly through the waveguide bore 211A from the end opening 211B to the end opening 211C), through the exit tube 242, and through the exit connector 278 to the liquid sample receiver 52.

Simultaneously, a beam of optical energy emitted from the lamp 22 of the source 20 is transmitted, in sequence, through the window 124, into the input fiber 222 through the end face 222A, through the fiber 222, into the waveguide bore 211A through the fiber end face 222B, through the liquid sample in the bore 211A, into the exit fiber 232 through the end face 232A, and through the fiber 232 to the input of the detector 30 through the fiber end face 232B. The liquid sample in the bore 211A serves as an optical core and the cladding layer 211 serves as an optical cladding providing total internal reflection. The waveguide 212 has an illuminated path length LP (i.e., the axial length of the column of liquid sample illuminated in the bore 211A) extending from the fiber end face 222A to the fiber end face 232A.

In an exemplary embodiment, the detector 30 is a PDA spectrometer including a photodiode array and a grating to divide an incident light beam into prescribed wave lengths (or ranges of wave lengths) and project the different wave lengths onto different respective photodiodes of the PDA. The liquid sample is axially illuminated by the source beam from the source 20. The illuminated liquid sample will absorb and thereby attenuate the light at different wave lengths in accordance with its composition. The voltage of each photodiode will be reduced in proportion to the reduction of its corresponding wave length in the light beam exiting the liquid sample through the optical fiber 232.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A liquid sample analyzer comprising:
a flow cell configured to receive a flow of a liquid sample from a liquid sample source;
a light source including a lamp configured to emit light to illuminate the flow of the liquid sample in the flow cell; and
a lamp temperature management system including:
an air flow generator operable to generate a turbulent air flow to cool the lamp;
a thermally conductive primary housing encapsulating the lamp such that a primary air gap is provided between the primary housing and the lamp; and
a thermally conductive secondary housing surrounding the primary housing and configured to deflect the turbulent air flow away from the primary housing;
wherein:
a buffer chamber is defined by and between the primary housing and the secondary housing;
the buffer chamber is fluidly sealed from the turbulent air flow generated by the air flow generator;
the primary housing defines a lamp chamber containing the lamp; and
the lamp chamber is fluidly sealed from the buffer chamber.

2. The liquid sample analyzer of claim 1 wherein the primary housing includes thermal fins extending into the buffer chamber to facilitate heat transfer from the lamp chamber to the buffer chamber.

3. The liquid sample analyzer of claim 1 wherein the lamp temperature management system is configured such that, in use, a laminar air flow is generated in the buffer chamber.

4. The liquid sample analyzer of claim 1 including a feed duct for directing the turbulent air flow at the secondary housing.

5. The liquid sample analyzer of claim 1 wherein:
the primary housing includes a window opening fluidly sealed by a transparent lens; and
the light source is configured to emit light from the lamp through the lens to the flow cell.

6. The liquid sample analyzer of claim 5 including a mirror disposed in the primary housing and configured to direct light from the lamp through the lens.

7. The liquid sample analyzer of claim 1 including a source optical fiber configured and operatively connected between the primary housing and the flow cell to transmit light from the lamp to the flow cell.

8. The liquid sample analyzer of claim 1 wherein the primary housing and the secondary housing are each formed of metal.

9. The liquid sample analyzer of claim 1 wherein the lamp is a deuterium lamp.

10. The liquid sample analyzer of claim 1 wherein:
the primary housing includes thermal fins extending into the buffer chamber to facilitate heat transfer from the lamp chamber to the buffer chamber;
the lamp temperature management system is configured such that, in use, a laminar air flow is generated in the buffer chamber;
the primary housing includes a window opening fluidly sealed by a transparent lens; and
the light source is configured to emit light from the lamp through the lens to the flow cell.

11. The liquid sample analyzer of claim 1 further including:
a spectrometer optically connected to the flow cell to receive light from the flow cell; and
a liquid sample source to supply the flow of the liquid sample to the flow cell.

12. A method for analyzing a liquid sample, the method comprising:

providing a liquid sample analyzer including:
- a flow cell configured to receive a flow of a liquid sample from a liquid sample source;
- a light source including a lamp configured to emit light to illuminate the flow of the liquid sample in the flow cell; and
- a lamp temperature management system including:
  - an air flow generator operable to generate a turbulent air flow to cool the lamp;
  - a thermally conductive primary housing encapsulating the lamp such that a primary air gap is provided between the primary housing and the lamp; and
  - a thermally conductive secondary housing surrounding the primary housing and configured to deflect the turbulent air flow away from the primary housing;

using the air flow generator, generating a turbulent air flow and directing the turbulent air flow onto the secondary housing to cool the secondary housing, thereby cooling the primary housing, and thereby cooling the lamp; wherein:
- a buffer chamber is defined by and between the primary housing and the secondary housing;
- the buffer chamber is fluidly sealed from the turbulent air flow generated by the air flow generator;
- the primary housing defines a lamp chamber containing the lamp; and
- the lamp chamber is fluidly sealed from the buffer chamber.

13. The method of claim 12 wherein the primary housing includes thermal fins extending into the buffer chamber to facilitate heat transfer from the lamp chamber to the buffer chamber.

14. The method of claim 12 wherein the lamp temperature management system is configured such that, in use, a laminar air flow is generated in the buffer chamber.

15. The liquid sample analyzer of claim 1 wherein the primary housing and the secondary housing are each formed of a material having a thermal conductivity in the range of from about 100 W/m-k to 250 W/m-k.

16. The method of claim 12 wherein the primary housing and the secondary housing are each formed of a material having a thermal conductivity in the range of from about 100 W/m-k to 250 W/m-k.

* * * * *